United States Patent [19]

Imbruce et al.

[11] 4,214,593
[45] Jul. 29, 1980

[54] ESOPHAGEAL PRESSURE MONITORING DEVICE

[75] Inventors: Richard Imbruce, Norwalk, Conn.; Nelson E. Leatherman, Chapel Hill, N.C.

[73] Assignee: Mallinckrodt, Inc., St. Louis, Mo.

[21] Appl. No.: 943,445

[22] Filed: Sep. 18, 1978

[51] Int. Cl.² .............................................. A61B 10/00
[52] U.S. Cl. .................................. 128/748; 128/780; 128/349 B; 128/348
[58] Field of Search ............... 128/658, 673, 720, 748, 128/780, 349 B, 350 R, 750

[56] References Cited

U.S. PATENT DOCUMENTS

| | | | |
|---|---|---|---|
| 550,238 | 11/1895 | Allen, Jr. .......................... | 128/349 B |
| 2,845,930 | 8/1958 | Brown .............................. | 128/349 B |
| 3,046,988 | 7/1962 | Moreau et al. ............... | 128/349 B X |
| 3,144,868 | 8/1964 | Jascalevich ...................... | 128/349 B |
| 3,429,314 | 2/1969 | Ericson ............................. | 128/349 R |
| 3,448,739 | 6/1969 | Stark et al. ...................... | 128/348 X |
| 3,625,793 | 12/1971 | Sheridan .......................... | 128/349 X |
| 3,636,940 | 1/1972 | Gravlee ............................ | 128/750 |
| 4,027,659 | 6/1977 | Slingluff .......................... | 128/658 |
| 4,100,246 | 7/1978 | Frisch .............................. | 128/349 B |
| 4,114,625 | 9/1978 | Onat ................................ | 128/349 B |

FOREIGN PATENT DOCUMENTS 790091 9/1935 France ..................................... 128/750

OTHER PUBLICATIONS

*Am. J. Surg.*; 124:262–269 (1972).
*J. Appl. Physiol.*; 23:433–438 (1967).
*J. Appl. Physiol.*; 26(3):330 (1969).
*Ann. Surg.*; 171(5):679–685 (1970).
*Surgery*; 70(2):280–287 (1971).
*J. Appl. Physiol*; 29:283–287 (1970).
*J. Appl. Physiol*; 37(4):600–603 (1974).
*J. Appl. Physiol*; 5:779 (1953).
*J. Appl. Physiol*; 38(3):411–417 (1975).
*J. Appl. Physiol*; 14:525 (1959).
*J. Lab. Clin. Med.*; 40:664 (1952).
*J. Lab. Clin. Men.*; 40:674–681 (1952).
*J. Appl. Physiol.*; 19:(2):207–211 (1964).

*Primary Examiner*—Kyle L. Howell
*Attorney, Agent, or Firm*—Carroll F. Palmer

[57] ABSTRACT

A device for monitoring esophageal pressure in patients comprises a nasogastric tube provided with an esophageal balloon cuff communicating through wallports with a secondary lumen that leads to an external connector tube through which continuous measurements of esophageal pressure can be made without interruption of the function of the nasogastric tube. The tube may include a tertiary lumen that serves to vent the major tube lumen at the distal end to prevent excessive vacuum from developing when suction is applied to the tube.

5 Claims, 5 Drawing Figures

ESOPHAGEAL PRESSURE MONITORING DEVICE

BACKGROUND OF THE INVENTION

1. Field of the Invention

This invention relates broadly to medico-surgical tube devices for monitoring intraesophageal pressure in a patient.

More particularly, it concerns an improved form of nasogastric tube provided with an esophageal balloon cuff and fluid conduction means permitting esophageal pressure to be monitored to determine lung compliance and respiratory work values in patients.

2. Description of the Prior Art

The use of esophageal balloons to measure intrapleural pressure in the study of lung mechanics was introduced in 1949 by Buytendijk. The technique employs an air-containing balloon sealed over a catheter which transmits balloon pressure to a low compliance manometer or pressure transducer. The catheter is usually intubated through a nare and positioned in the lower or middle third of the esophagus [*J. Appl. Physiol.* 14:525 (1959) and 19(2):207-211 (1964)].

Numerous studies have compared intrapleural pressures with those in the esophagus noting the differences and similarities under a variety of conditions in both normal and abnormal subjects [J. Lab. Clin. Med. 40:664 (1952) and 40:674-681 (1952)]. The results of these studies have shown that changes in intraesophageal pressure closely approximate changes in intrapleural pressure, but that absolute (gauge) pressures in the esophagus tend to be more positive than those in the pleural cavity, particularly when measurements are conducted in the supine position. Techniques for improving absolute pressure measurements have been described by several investigators [J. Appl. Physiol. 19(2):207-211 (1964); 29:283-287 (1970) and 37(4):600-603 (1974)]. The discrepancy between absolute pressures measured in the esophagus and pleural cavity, however, has not curtailed investigation of the mechanics of ventilation since pressure changes are of much greater significance than absolute pressures. Innumerable investigators have utilized esophageal balloons to characterize the mechanical properties of the lung in both health [J. Appl. Physiol. 5:779 (1953) and 38(3):411-417 (1975)], and in disease [J. Appl. Physiol. 23:433-438 (1967) and 26:330 (1969)] as well as in determining the work of breathing [Ann. Surg. 171(5):679-685 (1970)].

Despite the extensive volume of literature demonstrating acceptance and use of the esophageal balloon as a research and laboratory tool, there are few reports of its use as a monitoring tool in the clinical management of acutely ill patients [Surgery 70(2):280-287 (1971) and Am. J. Surg. 124:262-269 (1972)]. This limited use in the clinical environment has been due primarily to time consuming technical difficulties inherent in current procedures. In order to obtain the necessary serial or trend information concerning a patient's intrapleural pressure, the health care team has had to perform repeated esophageal intubations or make provisions for maintaining a double intubation of the esophagus, namely, an esophageal balloon catheter and a nasogastric tube.

In the clinical management of patients, it has been found that patients with respiratory problems, or that have a risk of developing such problems, frequently require nasogastric tubes. Also, nearly all patients requiring mechanical ventilation have nasogastric intubations as part of their routine clinical management. Hence, there exists a need for a nasogastric tube that can perform the additional function of allowing continuous or serial monitoring of esophageal pressure.

Aside from the field of esophageal catheter research, it is known to provide nasogastric tubes with a plurality of lumen, one of which may communicate with an inflation balloon on the catheter proximal of the distal end (U.S. Pat. Nos. 3,046,988 and 3,055,371). It is also known to use the balloon cuff on a catheter to measure pressures within a subject's body cavity during diagnostic procedure using the catheter (French Pat. No. 790,091). Also, multiple-lumen balloon-cuff catheters have been used for pressure measurement other than via the balloon-cuff (U.S. Pat. No. 3,448,739).

OBJECTS

A principal object of this invention is to provide new forms of nasogastric tubes that greatly facilitate monitoring esophageal pressure specifically in those patients requiring nasogastric intubation in their clinical management.

Another object is the provision of improvements in esophageal pressure monitoring devices.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished according to the present invention by forming an esophageal pressure monitoring device from a nasogastric tube that is provided with a secondary lumen formed in the tube, sealing an elongated balloon cuff to the outside of the tube at a central portion thereof, terminating the secondary lumen distally of the proximal end of the balloon cuff, providing at least one port through the wall of the tube communicating the secondary lumen with the interior of the balloon cuff for flow of fluid from the secondary lumen into and out of the balloon cuff, further providing an opening in the wall of the tube communicating with said secondary lumen and fixing a tube to said opening so that the tube may be connected to a low compliance manometer or pressure transducer to measure the pressure existing in the balloon cuff.

Preferably, the nasogastric tube has a tertiary lumen that runs, from a connector tube fixed to an opening into the tertiary lumen at the proximal end of the nasogastric tube, to near the distal end of such tube where it opens into the major lumen of the tube forming a vent to prevent excessive vacuum from developing when suction is applied to the tube via the major lumen.

This arrangement allows the balloon to be positioned above the cardiac sphincter while the distal end of the tube is positioned within the stomach. An opaque marker in the tube allows x-ray verification of position. The balloon is made of thin, flexible polyvinyl chloride plastic that will allow pressure changes acting on the external surface of the balloon to be adequately transmitted to the interior of the balloon and secondary lumen.

BRIEF DESCRIPTION OF THE DRAWINGS

A more complete understanding of the invention may be had by reference to the accompanying drawings in which.

DESCRIPTION OF THE PREFERRED EMBODIMENTS

Figure 1:
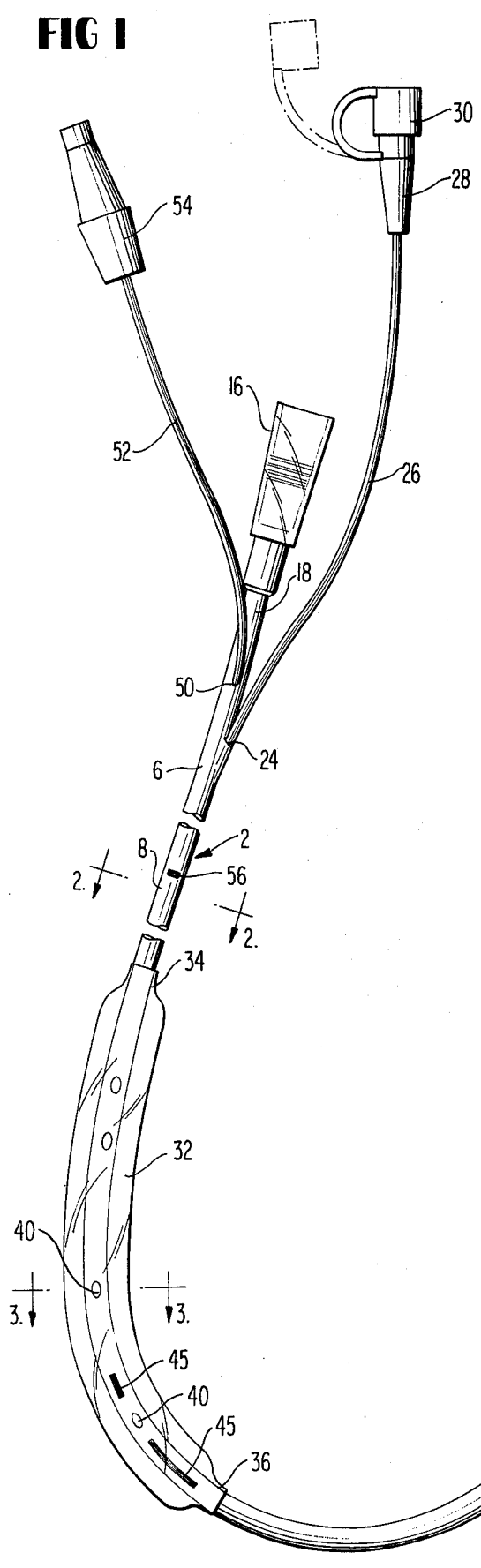
FIG. 1 is a fragmentary plan view of an esophageal pressure monitoring device in accordance with the invention.
Figure 2:
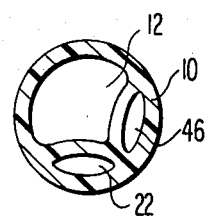
FIG. 2 is an enlarged, sectional view taken on the line 2—2 of FIG. 1.
Figure 3:
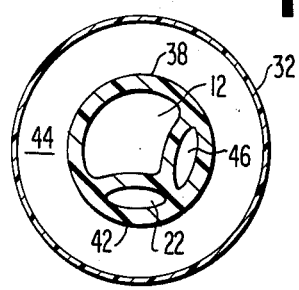
FIG. 3 is an enlarged, sectional view taken on the line 3—3 of FIG. 1.
Figure 4:
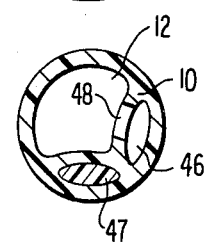
FIG. 4 is an enlarged, sectional view taken on the line 4—4 of FIG. 1.

Referring in detail to the drawings, the esophageal pressure monitoring device 2 of the invention comprises a distal end portion 4, proximal end portion 6 and central body portion 8 that joins the distal end portion 4 to the proximal end portion 6, said portions 4, 6 and 8 preferably being formed integrally as a nasogastric tube 10.

The tube 10 has a major lumen 12 extending centrally along it from a closed tip 14 that terminates the distal end portion 4 to connector means 16 which terminates the end 18 of the proximal end portion 6. The tube 10 has a plurality of side ports 20 in the distal end portion 4 that communicate the major lumen 12 with the exterior of the tube 10. Alternatively, the tip 14 of the tube 10 may be open-ended.

A secondary lumen 22 extends longitudinally along the tube 10. There is an opening 24 in the proximal end portion 6 of the tube 10 communicating with the secondary lumen 22 and a connector tube 26 is fixed into said opening 24 in any suitable manner, e.g., by the procedure disclosed in U.S. Pat. No. 3,625,793. The proximal end of the tube 26 may advantageously terminate with a female coupling 28 having an integral cap 30 and an opening (not shown) to receive the Luer tip of a syringe for introduction of fluid into the tube 26 and, in turn, the secondary lumen 22.

A balloon cuff 32 having a length substantially longer than its diameter is sealed at its proximal end 34 and distal end 36 to the outer surface 38 of the central body portion 8. Advantageously, the sealing is accomplished by application of solvent or cement between the cuff ends 34 and 36 and the surface 38, but any other sealing method, e.g., heat fusion, known or developed by the art may be used. The balloon cuff is formed of very thin, flexible rubber or plastic preferably by blow-molding, mandrel dipping or the like. Plastic material for the cuff may include silicone rubber, polyolefin, polyacrylates, etc. although plasticized polyvinyl chloride is preferred. A typical device would have a 14 FR size tube 10 and a balloon cuff 1.2 cm in diameter and 10 cm in length, with the end 36 positioned approximately 20 cm from the closed tip 14.

One or more ports 40 are formed through the wall 42 of the central body portion 8 communicating the secondary lumen 22 with the interior 44 of the balloon cuff 32 for flow of fluid from the secondary lumen 22 into or out of the cuff interior 44 for inflation or deflation of the cuff 32.

The secondary lumen 22 is closed at a point positioned distally of the proximal end 34 of the cuff 32. This lumen closing can be by fusion of the wall of tube 10 over the lumen 22 at the closed end 14 of the device 2. Alternatively, such closing can occur any where along the distal end portion 4 distally of at least one of the ports 40 so there will be fluid communication through a port 40 with the cuff interior 44, lumen 22 and tube 26 to the coupling 28.

Portions of rod 45 made of x-ray opaque plastic may be inserted in the secondary lumen to delineate the distal end 36 of the balloon cuff 32 by x-ray examination when the tube 10 is installed in a patient. Similarly, an x-ray marking 47 may be formed adjacent the tip 14 to delineate the distal end of tube 10 during use in a patient. The marking 47 may be a piece of x-ray opaque plastic rod which also serves as a plug for the distal end of lumen 22.

In the preferred forms of the devices 2, a tertiary lumen 46 is formed in the tube 10 extending longitudinally along the tube. The lumen 46 has an opening 48 in its distal end adjacent the closed tip 14 of the tube 10 to provide a passage into the major lumen 12 at its distal end to vent the lumen 12 and prevent excessive vacuum from developing in the tube when suction is applied to the major lumen 12.

There is an opening 50 in the proximal end portion 6 of tube 10 communicating with the tertiary lumen 46. A connector tube 52 is fixed, in comparable manner to tube 26, into the opening 50 for fluid flow between the lumen 46 and the tube 52. The distal end of tube 52 preferably has fixed thereto a tapered combination male/female coupling 54 for connection to equipment in accordance with established clinical practice.

One or more markings 56 of ink or the like may be applied to the surface of the tube 10 to enable a surgeon or other user of the device 2 to gauge the distance of intubation of the patient (not shown) by the device 2.

Figure 5:
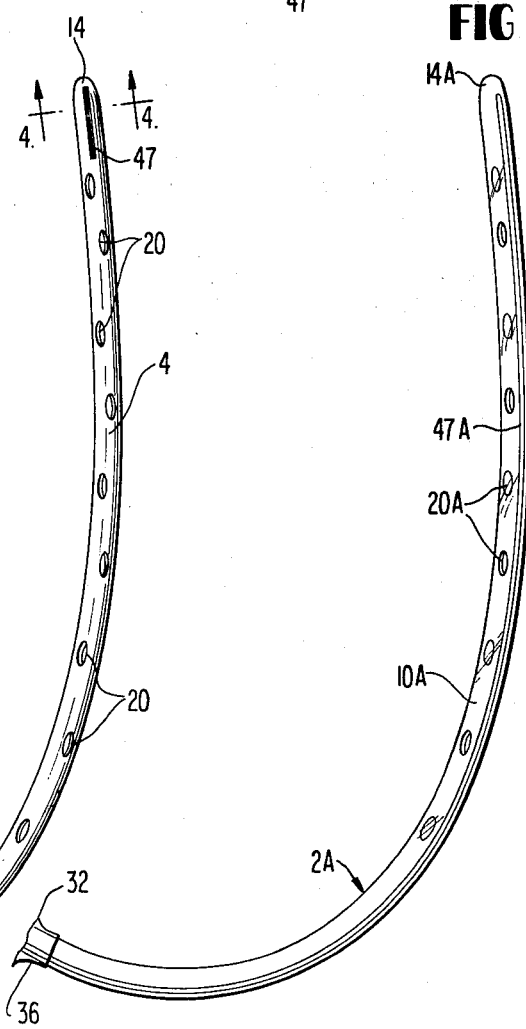
FIG. 5 is a fragmentary view of the distal end portion of an alternative form of a monitoring device of the invention.

The modification of device 2A shown in FIG. 5 differs from device 2 of FIG. 1 by having the x-ray opaque rod or filament 47A extend longitudinally along the tube 10A from the closed tip 14A up to the distal end 36 of the cuff 32 to provide a much longer x-ray marker for the device 2A as compared with marker 47 of device 2. The marker 47A may be formed by installation of a flexible filament or rod of x-ray opaque plastic into the secondary lumen 22 before the end 14A is closed by heat-fusion of the tube 10A at its end.

Esophageal pressure monitoring devices of the invention may be made from any material known or found to be useful for fabrication of such devices. Also they may be made in all sizes and styles required by the medical and related professions. Advantageously, they are packaged separately in suitable sleeve packages and sterilized by known procedures, e.g., exposure to ethylene oxide vapors or gamma radiation.

The method of use of the new devices of the invention reduces complications in the monitoring intraesophageal pressure according to established procedures. The patient is intubated in normal manner through a nare with the device 2 until the balloon cuff 32 is positioned above the patient's cardiac sphincter. The device construction then results in the distal end of tube 10 being within the patient's stomach. The x-ray opaque markers 45 and 47 or 47A allow x-ray verification of position. The connector 16 is coupled to conventional suctioning equipment and the balloon cuff 32 is inflated to within about 0.5 to 1.0 cc. of air by syringe application of air through the connector 28 and the connector is then joined to a low-compliance pressure transducer or comparable pressure measuring device. The static pressure-volume characteristics of the esophageal balloon 32 render the balloon exceptionally compliant over a volume range of 0–4 ml. This prevents the elastic properties of the balloon from altering the esophageal pressure measurement providing the balloon volume is approximately in the 0–4 ml. range.

The dynamic characteristics of the new balloon systems have been determined from both step response and sinusoidal frequency response tests. Step changes in applied pressure are complete within 10 ms after the step change is initiated. The results of sinusoidally forcing the system show that there is no attenuation or phase shift in the measured pressure for sinusoidal forcings in the range of 0–10 HZ. These characteristics demonstrate a fidelity more than adequate for monitoring esophageal pressure.

Using the new devices of the invention, measurements of various types may be readily accomplished, e.g., measurements of the work of breathing by patients receiving assist/control ventilation. By coupling with suitable instrumentation allowing on-line waveform presentation and analysis, ventilator waveform adjustment so as to provide the most efficient way to assist/control a patient with a ventilator. Numerous, other techniques of patient control and/or analysis can be devised using the new devices of the invention.

SUMMARY

A nasogastric tube with esophageal balloon has been described which greatly facilitates monitoring of esophageal pressure in patients normally requiring nasogastric intubation during hospital management. Since the nasogastric-esophageal balloon performs all the functions of both the common nasogastric tube and the esophageal balloon catheter, a single intubation of the device will allow continuous monitoring of esophageal pressure without interruption of the function of the nasogastric tube for as long as the patient is intubated. Serial measurements of esophageal pressure or pulmonary mechanics may thus be obtained without the need for repeated esophageal intubations.

The embodiments of the invention in which an exclusive property or privilege is claimed are defined as follows:

1. An esophageal pressure monitoring nasogastric tube comprising
   a distal end portion that terminates in a rounded tip,
   a proximal end portion that terminates in tube connector means,
   a central body portion joining the distal end portion to the proximal end portion,
   a major lumen extending within said tube from said tip to said tube connector means,
   a plurality of side ports through said distal end portion communicating with said major lumen,
   a secondary lumen extending longitudinally within said tube,
   a very thin balloon cuff having a length substantially longer than the diameter thereof sealed at its ends to the outside of said central body portion of said tube, said diameter being such that said balloon cuff can be appreciably inflated with about 0.5 to 1 cc of air and it is compliant over a volume range of 0 to 4 ml.,
   said secondary lumen being closed at a point positioned distally of the proximal end of said balloon cuff,
   at least one port through the wall of said central body portion communicating said secondary lumen with the interior of said balloon cuff for flow of fluid from said secondary lumen into said balloon cuff,
   a first opening in the wall of said proximal end portion of said tube communicating with said secondary lumen,
   a first connector tube fixed to said first opening for introduction of fluid into said secondary lumen,
   a tertiary lumen extending longitudinally within said tube,
   said tertiary lumen opening at its distal end into said major lumen adjacent said rounded tip of said tube providing a passage to vent said tube to prevent excessive vacuum from developing when suction is applied to said major lumen,
   a second opening in the wall of said proximal end portion of said tube communicating with said tertiary lumen, and
   a second connector tube fixed to said second opening for introduction of fluid into said tertiary lumen.

2. The device of claim 1 wherein an x-ray opaque filament is imbedded in the wall of said tube and extends from said end proximally along the tube.

3. The device of claim 1 wherein said second connector tube has a coupling fixed to its proximal end.

4. The device of claim 1 wherein there are three ports through the central body portion communicating said secondary lumen with said balloon cuff interior and said secondary lumen closed distal end is positioned distally of the most distal of said three ports.

5. The device of claim 1 wherein the cross-sectional area of said secondary lumen is at least as great as the cross-sectional area of said tertiary lumen.

* * * * *